United States Patent [19]

Lesser

[11] 4,210,592
[45] Jul. 1, 1980

[54] THIOPHOSPHORO-S-ACYLATED HYDRAZONES

[75] Inventor: Joseph H. Lesser, Beer Sheva, Israel

[73] Assignee: Makhteshim Chemical Works Ltd., Beer Sheva, Israel

[21] Appl. No.: 850,091

[22] Filed: Nov. 8, 1977

Related U.S. Application Data

[63] Continuation-in-part of Ser. No. 699,685, Jun. 25, 1976, abandoned.

[30] Foreign Application Priority Data

Jun. 27, 1975 [IL] Israel .................................. 47591

[51] Int. Cl.² ...................... C07D 307/46; C07F 9/165
[52] U.S. Cl. ............................... 260/347.2; 260/326.2; 260/345.7 R; 260/923; 424/200; 424/202; 424/203; 424/211; 546/22; 549/5; 549/6; 549/8
[58] Field of Search ............................ 260/347.2, 923; 424/211, 203

[56] References Cited

U.S. PATENT DOCUMENTS 3,518,327  6/1970  Fearing ................. 260/923

*Primary Examiner*—Anton H. Sutto
*Attorney, Agent, or Firm*—Browdy and Neimark

[57] ABSTRACT

The invention relates to compounds having the formula:

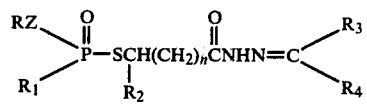

wherein
R is lower alkyl, cycloalkyl and aryl;
$R_1$ is lower alkyl, cycloalkyl, aryl and lower alkoxy;
$R_2$ is hydrogen, methyl, ethyl and

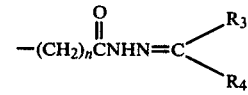

$R_3$ and $R_4$ are independently lower alkyl, cycloalkyl, aryl or a heterocyclic ring having 5 to 6 members at least 4 of which are carbons and one of which is selected from nitrogen, oxygen and sulfur;
$R_4$ may also be hydrogen, and $R_3$ and $R_4$ in combination may be part of a ring having 5 to 6 members at least 4 of which are carbons and the rest are selected from carbon, nitrogen, oxygen and sulfur;
Z is oxygen, sulfur, —NH or —NR; and
n is 0 or 1.

14 Claims, No Drawings

THIOPHOSPHORO-S-ACYLATED HYDRAZONES

This application is continuation-in-part application of Ser. No. 699,685 filed June 25, 1976, now abandoned.

FIELD OF THE INVENTION

This invention pertains to new organic chemical compounds, to their method of preparation, to new pesticidal compositions, and to a new method for controlling pests. The present invention is more particularly directed to new thiophosphoro-S-acylated hydrazones, and to new pesticidal compositions containing the same.

STATE OF THE PRIOR ART

Phosphoric and thiophosphoric acid esters have been known for a long time to possess pesticidal properties [C. Fest and K. J. Schmidt, *The Chemistry of Organophosphorous Pesticides,* Springer-Verlag, New York, 1973]. Within this large group, compounds containing both the thiophosphoric group and the N,N-dialkylhydride group [—NH—NR$_2$R$_2$] are known, such compounds are described in Belgian patent applications Nos. 749,407; 749,408 and 749,409 assigned to Farbenfabriken Bayer AG.; Belgian patent application No. 766,595 and Netherlands patent application No. 7,105,575 assigned to Esso Research and Engineering Co.; and U.S. Pat. No. 3,518,327 issued to R. B. Fearing and assigned to Stauffer Chemical Co.

All these patents disclose thiophosphoro-or phosphono-acetyl hydrazides having in common the structure $$\underset{>}{\overset{X}{\underset{\|}{P}}}-SCH_2\overset{O}{\underset{\|}{C}}NHN\underset{R}{\overset{R}{<}}$$

wherein the R groups are attached to the nitrogen via single bonds; these compounds are claimed to be useful insecticides or acaricides.

Of particular notice is U.S. Pat. No. 3,518,327 which, while broadly disclosing and claiming thio- and dithiophosphoroacetyl hydrazides, exemplifies only dithiocompounds. This patent further discloses dithiophosphoroacetyl methylene and ethylidene hydrazide and exemplifies these with the dithio- compound of the formula $$\underset{CH_3O}{\overset{CH_3O}{>}}\overset{S}{\underset{\|}{P}}-SCH_2\overset{O}{\underset{\|}{C}}NHN=CH_2$$

for which no test data is presented as to its pesticidal activity.

U.S. Pat. No. 2,965,667, issued to H. Tolkmith and assigned to the Dow Chemical Co., discloses phosphorohydrazidothioates where the phosphorous is directly bonded to the hydrazido nitrogen. These compounds are stated to be useful as intermediates for the preparation of more complex organic derivatives and also as parasiticides for the control of mite, insect and bacterial organisms such as flies, southern army worms and aphids.

SUMMARY OF THE INVENTION

The invention relates to a new class of thiophosphoro-S-acylated hydrazones having pesticidal activity, particularly against aphids, and mites. The new thiophosphoro-S-acylated hydrazones can be represented by the following formula:

$$\underset{R_1}{\overset{RZ}{>}}\overset{O}{\underset{\|}{P}}-SCH(CH_2)_n\overset{O}{\underset{\|}{C}}NHN=C\underset{R_4}{\overset{R_3}{<}}$$
$$\qquad\qquad\quad\overset{|}{R_2}$$

wherein

R is lower alkyl, cycloalkyl and aryl;

R$_1$ is lower alkyl, cycloalkyl, aryl and lower alkoxy;

R$_2$ is hydrogen, methyl, ethyl and $$-(CH_2)_n\overset{O}{\underset{\|}{C}}NHN=C\underset{R_4}{\overset{R_3}{<}}$$

R$_3$ and R$_4$ are independently lower alkyl, cycloalkyl, aryl or a heterocyclic ring having 5 to 6 members at least 4 of which are carbons and one of which is selected from nitrogen, oxygen and sulfur.

R$_4$ may also be hydrogen, and R$_3$ and R$_4$ in combination may be part of a ring having 5 to 6 members at least 4 of which are carbons and the rest selected from carbon, nitrogen, oxygen and sulfur;

Z is oxygen, sulfur, —NH or —NR; and n is 0 or 1.

The new thiophosphoro-S-acylated hydrazones of this invention are generally active pesticides but have been found to be particularly active against aphids and mites. Their activity against aphids is particularly surprising and unexpected when compared with the corresponding dithiophosphoro-5-acyl hydrazones.

The lower alkyl radicals suitable for R, R$_1$, R$_3$ and R$_4$ are the straight and branched chain aliphatic radicals having from 1 to 8 carbons and include for example methyl, ethyl, n-propyl, isopropyl, n-butyl, s-butyl, iso-butyl, tert-butyl, pentyl, hexyl,heptyl, octyl and their respective isomers. Similarly, the lower alkoxy radicals suitable for R$_1$ are the straight and branched chain radicals having from 1 to 8 carbons including methoxy, ethoxy, n-propoxy, isopropoxy, butoxy, amyloxy, hexoxy, heptoxy and octoxy and the like. Preferably R and R$_1$ are methyl or ethyl.

Cycloalkyl radicals suitable for R, R$_1$, R$_3$ and R$_4$ are cyclopropyl, cyclobutyl, cyclopentyl and cyclohexyl. Aryl radicals suitable for R,R$_1$, R$_3$ and R$_4$ are phenyl, halogen substituted phenyl, lower alkyl substituted phenyl and nitrophenyl. These include, for example, 3, chlorophenyl, 3,5-dichlorophenyl, 4-bromophenyl, 4-fluorophenyl, tolyl, xylyl, 4-ethylphenyl, 4-isopropylphenyl,t-butylphenyl, 4-nitrophenyl and 3,5-dinitrophenyl.

Heterocyclic rings having 5 to 6 members at least 4 of which are carbons and one of which is selected from nitrogen, oxygen and sulfur, suitable for R$_3$ and R$_4$ are thiophene, furane, tetrahydrofurane, pyridine, pyrrole, and the like, preferably, however, furane.

Examples of rings where R$_3$ and R$_4$ in combination form part of a 5 to 6 member ring having at least 4 carbon atoms and the rest being selected from carbon, nitrogen, oxygen, and sulfur, are cyclopentane, cyclohexane, cyclohexene, cyclopentadiene, tetrahydrofurane,

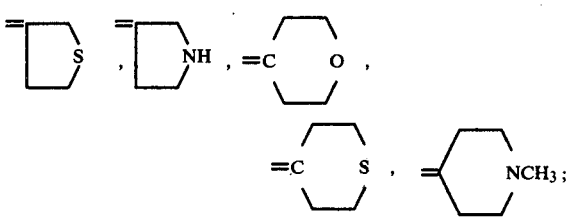

preferred compounds are those where $R_3$ is a lower alkyl group of at least two carbon atoms or furyl.

The new thiophosphoro S-acylated hydrazones of this invention may be prepared by reacting a salt having the formula

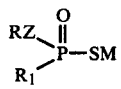

where R, $R_1$, and Z, have the meanings stated above, and M is an alkali or alkaline earth metal or ammonium ion, with a haloacyl hydrazone of the formula

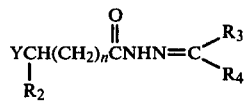

where $R_2$, $R_3$, $R_4$, and n have the meanings stated above, and Y stands for halogen, preferably chlorine. The reaction is advantageously effected in a solvent such as benzene, toluene, chlorinated hydrocarbons, acetonitrile, tetrahydrofurane, and other organic solvents which do not react with the reactants. The haloacyl hydrazones may be added to the solution of the salt in the form of a solid or as a solution in a suitable solvent. The temperature of the reaction mixture may be as low as $-10°$ C. and as high as $90°$ C., with a preferred range of $10°-65°$ C. The stoichiometry of the reaction requires one molecular equivalent of the salt for each mole of haloacyl hydrazone. However, a slight molar excess of the salt is preferred, although an excess of either reactant can be used if desired.

The new thiophosphoro-S-acylated hydrazones are recovered from the reaction mixture and purified by conventional methods. In cases when the product is a solid it can be filtered, washed free of by-product and unreacted starting materials, and recrystallized from a suitable solvent, e.g. ether, petroleum ether, hexane, benzene, pentane, cyclohexane, and the like.

The haloacyl hydrazone starting materials can be prepared by known methods. Illustratively they can be prepared by reacting equimolar amounts of the ester of halocarboxylic acid and hydrazine hydrate and then treating with an equivalent amount of a carbonyl compound according to the method of Ito and Narusawa [Bull. Soc. Jap., 43(1970)2257 (C.A., 73:87122v)].

The novel thiophosphoro-S-acylated hydrazones of this invention can be converted into the usual formulations, wuch as solutions, emulsions, suspensions, powders, pastes and granulates. These may be produced in known manner, for example by mixing the active compounds with extenders, that is, liquid or solid diluents or carriers, optionally with the use of surface-active agents, that is, emulsifying agents and/or dispersing agents. In the case of the use of water as an extender, organic solvents can, for example, also be used as auxiliary solvents.

As liquid diluents or carriers, there can be used aromatic hydrocarbons, such as xylenes or benzene; chlorinated aromatic hydrocarbons such as chlorobenzenes; paraffins, such as mineral oil fractions; alcohols such as methanol or butanol; or strongly polar solvents such as dimethyl formamide or dimethyl sulphoxide, as well as water.

As solid diluents or carriers, there can be used ground natural minerals, such as kaolins, clays, talc or chalk, or ground synthetic minerals, such as highly-dispersed silicic acid or silicates.

Examples of emulsifying agents include non-ionic and anionic emulsifiers, such as polyoxyethylene-fatty acid esters, polyoxyethylene-fatty alcohol ethers, for example alkylarylpolyglycol ethers, alkyl sulphonates and aryl sulphonates; examples of dispersing agents include lignin, sulphite waste liquors and methyl cellulose.

The active compounds according to the invention may be present in the formulation in admixture with other active compounds, such as other insecticides or fungicides.

The formulations contain, in general, from 0.1 to 95, preferably 0.5 to 90, percent by weight of active compound.

The active compounds may be used as such or in the form of their formulations prepared therefrom, such as ready-to-use solutions, emulsifiable concentrations, emulsions, suspensions, spray powders, pastes, soluble powders, dusting agents and granulates. Applications may take place in the usual manner, for example by watering, squirting, atomising, vaporisation, fumigation, scattering or dusting.

The invention, therefore, provides pesticidal composition containing as active ingredient a compound according to the invention in admixture with a solid diluent or carrier or in admixture with a liquid diluent or carrier containing a surface-active agent.

The invention also provides a method of combating insect or miticide pests which comprises applying to the pests or a habitat thereof (such as an area of agriculture) a compound according to the invention alone or in the form of a composition containing as active ingredient a compound according to the invention in admixture with a solid or liquid diluent or carrier.

EXAMPLE 1

To a solution of 14.0 g (0.075 mole) ammonium 0,0-diethylthiophosphorate in 125 ml acetonitrile was added, dropwise, over a period of thirty minutes, a solution of 10.0 g (0.05 mole) chloroacetyl-α-phenylhydrazone in 125 ml tetrahydrofurane. The reaction mixture was then heated to 40° C. for two hours, cooled to room temperature, filtered, and the volatiles removed from the filtrate under reduced pressure. The residue was dissolved in 200 ml chloroform, washed with five percent aqueous bicarbonate (2×25 ml) and water (1×50 ml), and then dried over anhydrous sodium sulfate. Filtering and removing the chloroform under reduced pressure afforded 17.5 g (80%) of 0,0-diethylthiophosphoro-S-acetyl-α-phenylhydrazone, a pale yellow-viscous liquid, $n_D^{27} = 1.571$.

EXAMPLE 2

To a solution of 9.3 g (0.05 mole) ammonium 0,0-diethylthiophosphorate in 150 ml acetonitrile was added, dropwise, a solution of 10.5 g (0.05 mole) chloroacetyl-α-phenylhydrazone in 150 ml of acetonitile over a period of thirty minutes. The reaction mixture was then heated to 40° C. for two hours, cooled to room temperature, filtered, and the volatiles removed from the filtrate via reduced pressure. The residue was dissolved in 200 ml chloroform, washed with five percent aqueous bicarbonate (2×50 ml) and water (1×50 ml), and then dried over anhydrous sodium sulfate. Filtering and removing the chloroform under reduced pressure afforded 9 g (50%) of a cream colored solid which was recrystallized from hexane to yield 0,0-diethylthiophosphoro-S-acetyl-α-methyl-α-phenylhydrazone, a solid with melting point of 79°-80° C.

EXAMPLE 3

To a solution of 3.0 g (0.016 mole) ammonium 0,0-diethylthiophosphorate in 100 ml acetonitrile was added, dropwise, over a period of one hour, a solution of 15.3 g (0.10 mole) chloroacetyl-α,α-dimethylhydrazone in 100 ml acetonitrile. The reaction mixture was then stirred at room temperature for an additional 18 hours, filtered, and the solvent removed under reduced pressure. The residue was dissolved in 200 ml chloroform, washed with water (3×30 ml) and five percent aqueous bicarbonate (3×30 ml, and then dried over anhydrous sodium sulfate. Filtering and removing the chloroform under reduced pressure afforded 12.7 g (90%) of 0,0-diethylthiophosphoro-S-acetyl-α,α-dimethylhydrazone, a slightly yellow viscous piquid.

EXAMPLE 4

To a solution of 10.5 g (0.069 mole) sodium 0,0-dimethylthiophosphorate in 200 ml acetonitrile was added, dropwise, over a period of two hours, a solution of 10.5 g (0.055 mole) chloroacetyl-α-methyl-α-t-butylhydrazone in 200 ml acetonitrile. The reaction was stirred at room temperature for an additional twenty hours, then at 40° C. for four hours, and the solvent removed under reduced pressure. The residue was dissolved in 100 ml chloroform washed with water (4×25 ml) and dried over anhydrous sodium sulfate. Filtering and removing the chloroform under reduced pressure, and recrystallizing the product from ether/pentene to afford 14.7 g of 0,0-dimethyl thiophosphoro-S-acetyl-α-methyl-α-t-butylhydrazone, a white crystalline product with a melting point of 65.5°-68.5° C.

EXAMPLE 5

To a solution of 9.45 g (0.06 mole)sodium 0,0-dimethyl-thio phosphorate in 200 ml acetonitrile was added, dropwise, over a period of an hour, a solution of 13.2 g (0.05 mole) chloroacetyl-α-(3,4-dichlorophenyl)-hydrazone in 200 ml acetonitrile. The reaction mixture was then stirred ar room temperature for an additional twenty hours, filtered, and the solvent removed under reduced pressure. The residue was dissolved in 200 ml chloroform. washed with water (2×25 ml) and five percent aqueous sodium bicarbonate (1×25 ml), and then dried over anhydrous sodium sulfate. Filtering, removing the residue from cyclohexane/ether (1:1)afforded 10.3 g of 0,0-dimethylthiophosphoro-S-acetyl-α-(3,4-dichlorophenyl)-hydrazone, a white crystalline product with a melting point of 99°-100° C.

EXAMPLE 6

To a solution of 10.77 g (0.058 mole) ammonium 0,0-diethylthiophosphorate in 100 ml tetrahydrofuran was added, dropwise, over a period of thirty minutes, a solution of 9.33 g (0.05 mole) chloroacetyl-α-(2-furan)-hydrazone in 200 ml tetrahydrofuran. The reaction mixture was allowed to stand overnight at room temperature and then heated at 40° C. for two hours. The mixture was then filtered and the solvent removed under reduced pressure. The residue was dissolved in 200 ml chloroform, washed with water (2×50 ml) and five percent aqueous bucarbonate (3×50 ml), and the dried over anhydrous sodium sulfate. Filtering, removing the chloroform under reduced pressure, and recrystallizing the residue from ether afforded 15.5 g of 0,0-diethylthiophosphoro-S-acetyl-α-(2-furan)-hydrazone, a grey crystalline product with a melting point of 72°-82° C.

EXAMPLES 7-13

Following the precedure of Example 1 but substituting the appropriate haloacetyl hydrazone and 0,0-dialkylthiophosphorate salt, compounds 7-13 were prepared. The melting points and analysis of compounds 1-13 are tabulated in Table 1.

TABLE 1

ANALYSIS OF O,O-DIALKYL THIOPHOSPHORO-S-ACETYL HYDRAZONES: $(RO)_2\overset{O}{\underset{\|}{P}}SCH_2\overset{O}{\underset{\|}{C}}NHN=V$

| Example Number | R | V | Melting Point (°C.) | CALCULATED (%) | | | | | FOUND (%) | | | | |
|---|---|---|---|---|---|---|---|---|---|---|---|---|---|
| | | | | C | H | N | P | S | C | H | N | P | S |
| 1 | C2H5 | C(H)C6H5 | liquid | 47.30 | 5.79 | 8.49 | 9.38 | | 47.03 | 6.03 | 8.84 | 8.49 | |
| 2 | C2H5 | C(CH3)C6H5 | 79-80 | 48.80 | 6.17 | 8.13 | | | 49.07 | 6.43 | 7.92 | | |
| 3 | C2H5 | C(CH3)2 | liquid | | 6.79 | 9.93 | 10.98 | | | 6.04 | 8.91 | 10.55 | |
| 4 | CH3 | C(CH3)C(CH3)3 | 65.5-68.5 | 40.58 | 7.15 | 9.46 | 10.46 | 10.83 | 38.46 | 6.87 | 10.00 | 9.01 | 9.40 |
| 5 | CH3 | CH(3,4-Cl2C6H3) | 99-100 | 35.61 | 3.53 | 7.55 | 9.35 | 19.11 $^a$ | 35.41 | 3.77 | 7.18 | 8.66 | 19.23 $^a$ |
| 6 | C2H5 | C(H)—  | 72-82 | 41.29 | 5.35 | 8.75 | 9.68 | 10.02 | 41.56 | 5.11 | 9.08 | 8.78 | 9.86 |
| 7 | C2H5 | C(H)CH3 | liquid | 35.79 | 6.38 | | | | 34.40 | 6.24 | | | |
| 8 | C2H5 | C(CH3)C2H5 | liquid | 40.58 | 7.15 | 9.46 | 10.46 | 10.83 | 38.14 | 6.88 | 9.18 | 10.66 | 9.54 |
| 9 | CH3 | C(CH3)CH(CH3)2 | liquid | 38.33 | 6.79 | 9.98 | 10.98 | 11.37 | 36.25 | 6.98 | 9.96 | 11.26 | 12.24 |
| 10 | C2H5 | C(CH3)CH(CH3)2 | liquid | 42.62 | 7.48 | 9.04 | 10.34 | 9.99 | 41.70 | 7.45 | 9.32 | 10.53 | 9.04 |
| 11 | CH3 | CH(4-ClC6H5) | 166-171 | | 4.19 | 8.32 | | | | 3.95 | 9.86 | | |
| 12 | C2H5 | CH(3,4-Cl2C6H3) | liquid | | 6.29 | 6.66 | | | | 7.02 | 7.76 | | |

TABLE 1-continued

ANALYSIS OF O,O-DIALKYL THIOPHOSPHORO-S-ACETYL HYDRAZONES: $(RO)_2\overset{O}{\overset{\|}{P}}SCH_2\overset{O}{\overset{\|}{C}}NHN=V$

| Example Number | R | V | Melting Point (°C.) | CALCULATED (%) | | | | | FOUND (%) | | | | |
|---|---|---|---|---|---|---|---|---|---|---|---|---|---|
| | | | | C | H | N | P | S | C | H | N | P | S |
| 13 | CH$_3$ | C(H)⟨furyl⟩ | liquid | | 4.49 | 9.59 | | | | 4.85 | 10.13 | | |

Following the procedure of Example 1 but substituting the appropriate haloacetyl hydrazone and O,O-dialkylthio-phosphorate salt, the following compounds were prepared whose NMR and infrared spectra were in accordance with the expected structures:

Example 14: (CH$_3$O)$_2$P(O)SCH$_2$C(O)NHN=C(CH$_3$)C$_2$H$_5$
Example 15: (C$_2$H$_5$O)$_2$P(O)SCH$_2$C(O)NHN=C(H)CH(CH$_3$)$_2$
Example 16: (CH$_3$O)$_2$P(O)SCH$_2$C(O)NHN=C(H)C$_6$H$_5$
Example 17: (C$_2$H$_5$O)$_2$P(O)SCH$_2$C(O)NHN=CH(4-ClC$_6$H$_4$)
Example 18: (C$_2$H$_5$O)$_2$P(O)SCH$_2$C(O)NHN=C(CH$_3$)C(CH$_3$)$_3$ Similarly, the following compounds can be prepared by substituting the appropriate haloacyl hydrazone in the reaction:

$$(CH_3O)_2P(O)SCHC(O)NHN=C(CH_3)_2$$
$$\quad\quad\quad |$$
$$\quad\quad CH_2C(O)NHN=C(CH_3)_2$$

$$(C_2H_5O)_2P(O)SCHC(O)NHN=C(CH_3)C_2H_5$$
$$\quad\quad\quad |$$
$$\quad\quad CH_3$$

$$(CH_3O)_2P(O)SCHC(O)NHN=C(CH_3)C_2H_5$$
$$\quad\quad\quad |$$
$$\quad\quad C_2H_5$$

$(CH_3O)_2P(O)SCH[C(O)NHN=CH(C_2H_5)]_2$
$(C_2H_5O)_2P(O)SCH[C(O)NHN=CH(C_2H_5)]_2$

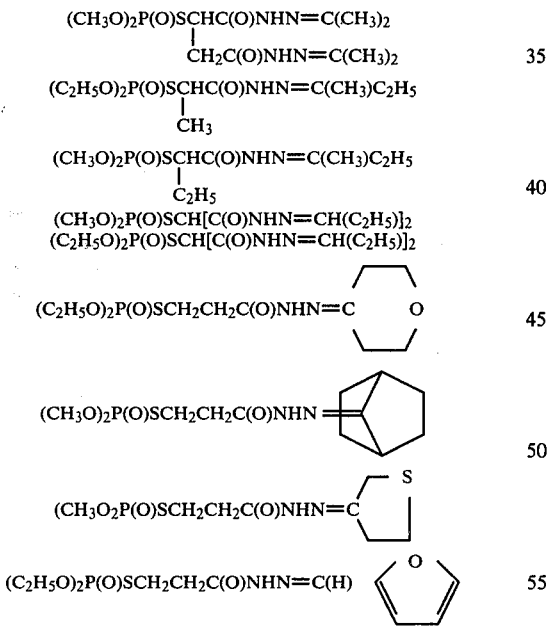

Following the procedure of Example 1, but substituting the appropriate thio-phosporous or -phosphoramidous acid ester salts for ammonium O,O-diethylthiophosphorate, the following compounds can be prepared:

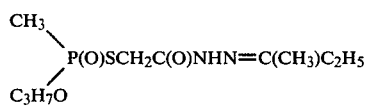

-continued

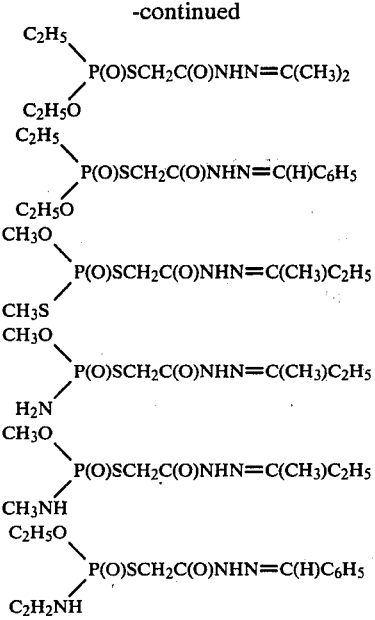

EXAMPLE 19

Tests were conducted to determine the effect of these compounds against *Myzus persicae* (aphids) in the following manner:

The compounds were dissolved in 10 ml acetone and diluted to 250 ml with distilled water. To this solution was added three drops of "Tween-80" as a wetting agent. Once a stable emulsion or solution was obtained, two radish leaves were dipped into it and left to dry. Then five discs of 2 cm diameter were cut from these leaves and placed with their underside uppermost, on wet cotton in a petri dish. Five large Myzus nymphs were placed on each disc and were examined for mortality after 24 hours, 48 hours, and five days from treatment. Controls were also set up containing leaf discs cut from leaves treated with a control (acetone, water, and "Tween 80" but no active ingredient). All dishes were covered with perforated lids which retained the insects but permitted enough gaseous exchange to prevent excessive condensation. The tests were held in a greenhouse cubicle at 18° C. The percent control afforded by the compounds of the present invention are listed in Table 2 at various concentrations.

EXAMPLE 20

Compounds according to the invention have been tested on spider mites in the following manner.

Candidate samples are formulated in acetone and emulsifier to improve the wetting properties. If solubility is a problem, the samples are wet ball milled. Excised lima bean plants are infested with 50 to 100 adult strawberry spider mites prior to testing. Adult mortality were noted; and are listed as percent control at various concentrations in Table 2.

TABLE 2
MORTALITY AGAINST APHIDS AND MITES

| Compound of Example | Concentration (p.p.m) | Percent Mortality Aphids | Percent Mortality Mites |
|---|---|---|---|
| 1 | 500 | 72 | 20 |
| 3 | 100 | 100 | 100 |
| 4 | 100 | 100 | 100 |
| 5 | 100 | 100 | 100 |
| 6 | 100 | 100 | 100 |
| 7 | 500 | 80 | 14 |
| 9 | 100 | 90 | — |
| 9 | 250 | — | 100 |
| 12 | 100 | 100 | 100 |
| 13 | 250 | 100 | — |
| 13 | 100 | — | 96 |
| 14 | 100 | 100 | 100 |
| 15 | 100 | 90 | 98 |
| 16 | 500 | 88 | 22 |
| 17 | 500 | 76 | 30 |
| 18 | 100 | 100 | 100 |

EXAMPLE 21

The activity of the new thiophosphoro-S-acylated hydrazones was compared with the activity of the corresponding dithiophosphoro-S-acylated hydrazones against aphids following procedure of Example 19. The results, as percent mortality, are listed in Table 3; and clearly show unexpectedly high activity for the thiophosphoro-S-acylated hydrazone compounds of the present invention.

The foregoing description is given for clearness of understanding only and no unnecessary limitations should be understood, therefrom, as modifications will be obvious to those skilled in the art.

MORTALITY OF APHIDS BY $(RO)_2\overset{X}{\overset{\|}{P}}SCH_2\overset{O}{\overset{\|}{C}}NHN=V$

| R | V | Concentration (p.p.m.) | Percent Mortality X=O | X=S |
|---|---|---|---|---|
| $C_2H_5$ | $C(H)C_6H_5$ | 500 | 72 | 0 |
| $C_2H_5$ | $C(CH_3)_2$ | 100 | 100 | 28 |
| $CH_3$ | $CH(3,4-Cl_2C_6H_3)$ | 100 | 100 | 0 |
| $C_2H_5$ | CH—furan | 100 | 100 | 20 |
| $C_2H_5$ | $C(H)CH_3$ | 500 | 80 | 0 |
| $CH_3$ | $C(CH_3)CH(CH_3)_2$ | 100 | 90 | 0 |
| $C_2H_5$ | $CH(3,4-Cl_2C_6H_3)$ | 100 | 100 | 0 |
| $CH_3$ | CH—furan | 250 | 100 | 20 |
| $CH_3$ | $C(CH_3)C_2H_5$ | 100 | 100 | 0 |
| $C_2H_5$ | $C(H)CH(CH_3)_2$ | 100 | 90 | 0 |

MORTALITY OF APHIDS BY $(RO)_2\overset{X}{\overset{\|}{P}}SCH_2\overset{O}{\overset{\|}{C}}NHN=V$
-continued

| R | V | Concentration (p.p.m.) | Percent Mortality X=O | X=S |
|---|---|---|---|---|
| $CH_3$ | $C(H)C_6H_5$ | 500 | 88 | 8 |
| $C_2H_5$ | $CH(4-ClC_6H_4)$ | 500 | 76 | 4 |

What we claim is:

1. A compound selected from the group consisting of
O,O-diethylthiophosphoro-S-acetyl-α-phenylhydrazone;
O,O-diethylthiophosphoro-S-acetyl-α-methyl-α-phenylhydrazone;
O,O-diethylthiophosphoro-S-acetyl-α,α-dimethylhydrazone;
O,O-dimethylthiophosphoro-S-acetyl-α-methyl-α-t-butylhydrazone;
O,O-dimethylthiophosphoro-S-acetyl-α-(3,4-dichlorophenyl)-hydrazone;
O,O-diethylthiophosphoro-S-acetyl-α-(2-furan)-hydrazone;
O,O-diethylthiophosphoro-S-acetyl-α-methylhydrazone;
O,O-diethylthiophosphoro-S-acetyl-α-methyl-α-ethylhydrazone;
O,O-dimethylthiophosphoro-S-acetyl-α-methyl-α-isopropylhydrazone;
O,O-diethylthiophosphoro-S-acetyl-α-methyl-α-isopropylhydrazone;
O,O-dimethylthiophosphoro-S-acetyl-α-(4-chlorophenyl)-hydrazone;
O,O-diethylthiophosphoro-S-acetyl-α-(3,4-dichlorophenyl)-hydrazone; and
O,O-dimethylthiophosphoro-S-acetyl-α-(2-furan)-hydrazone.

2. A compound of claim 1, O,O-diethylthiophosphoro-S-acetyl-α-phenylhydrazone.
3. A compound of claim 1, O,O-diethylthiophosphoro-S-acetyl-α-methyl-α-phenylhydrazone.
4. A compound of claim 1, O,O-diethylthiophosphoro-S-acetyl-α,α-dimethylhydrazone.
5. A compound of claim 1, O,O-dimethylthiophosphoro-S-acetyl-α-methyl-α-t-butylhydrazone.
6. A compound of claim 1, O,O-dimethylthiophosphoro-S-acetyl-α-(3,4-dichlorophenyl)-hydrazone.
7. A compound of claim 1, O,O-diethylthiophosphoro-S-acetyl-α-(2-furan)-hydrazone.
8. A compound of claim 1, O,O-diethylthiophosphoro-S-acetyl-α-methylhydrazone.
9. A compound of claim 1, O,O-diethylthiophosphoro-S-acetyl-α-methyl-α-ethylhydrazone.
10. A compound of claim 1, O,O-dimethylthiophosphoro-S-acetyl-α-methyl-α-iso-propylhydrazone.
11. A compound of claim 1, O,O-diethylthiophosphoro-S-acetyl-α-methyl-α-iso-propylhydrazone.
12. A compound of claim 1, O,O-dimethylthiophosphoro-S-acetyl-α-(4-chlorophenyl)-hydrazone.
13. A compound of claim 1, O,O-diethylthiophosphoro-S-acetyl-α-(3,4-dichlorophenyl)-hydrazone.
14. A compound of claim 1, O,O-dimethylthiophosphoro-S-acetyl-α-(2-furan)-hydrazone.